United States Patent [19]

Weinstock

[11] 3,947,580

[45] Mar. 30, 1976

[54] ANTI-ARTHRITIC COMPOSITIONS COMPRISING N-HETEROCYCLIC PULVINIC ACID AMIDES AND METHODS OF PRODUCING ANTI-ARTHRITIC ACTIVITY

[75] Inventor: Joseph Weinstock, Phoenixville, Pa.

[73] Assignee: SmithKline Corporation, Philadelphia, Pa.

[22] Filed: Mar. 27, 1975

[21] Appl. No.: 562,628

Related U.S. Application Data

[62] Division of Ser. No. 393,861, Sept. 4, 1973, Pat. No. 3,895,021.

[52] U.S. Cl. ............... 424/270; 424/250; 424/263; 424/272; 424/273
[51] Int. Cl.$^2$ ........................................ A61K 31/425
[58] Field of Search ........... 424/250, 263, 270, 272, 424/273

Primary Examiner—Stanley J. Friedman
Attorney, Agent, or Firm—Janice E. Williams; Richard D. Foggio; William H. Edgerton

[57] ABSTRACT

N-Heterocyclic pulvinic acid amides having antiarthritic activity are prepared by treating the corresponding pulvinic acid with a heterocyclic amine.

18 Claims, No Drawings

ANTI-ARTHRITIC COMPOSITIONS COMPRISING N-HETEROCYCLIC PULVINIC ACID AMIDES AND METHODS OF PRODUCING ANTI-ARTHRITIC ACTIVITY

This is a division of application Ser. No. 393,861, filed Sept. 4, 1973, now U.S. Pat. No. 3,895,021.

This invention relates to novel N-heterocyclic pulvinic acid amides which have useful pharmacological activity. More specifically, the compounds of this invention have anti-arthritic activity as measured by their ability to inhibit adjuvant-induced polyarthritis in rats.

The compounds of this invention are represented by the following structural formula:

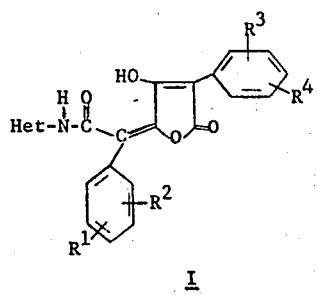

I in which:

$R^1$, $R^2$, $R^3$ and $R^4$ are each hydrogen, lower alkyl of from one to four carbon atoms, lower alkoxy of from one to four carbon atoms, phenyl, phenoxy, halogen, fluoroalkyl, hydroxy or, taken together in adjacent positions, methylenedioxy; and Het is a heterocyclic moiety of the formula

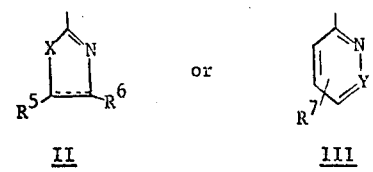

II    or    III in which:

X is S, NH or O;
Y is N or CH;
$R^5$ and $R^6$ are hydrogen, methyl or halogen, or together form a 1,2-benzo radical;
$R^7$ is hydrogen, methyl or halogen; and
⁓ indicates an optional double bond.

In the compounds represented by formula I, the substituents on the $R^3$, $R^4$-containing ring are designated by a prime ('). As used herein, halogen refers to fluoro, chloro and bromo; lower alkyl and lower alkoxy may be straight or branched chain moieties; and fluoroalkyl is preferably trifluoromethyl.

Preferred compounds of this invention are represented by formula I where Het is substituted or unsubstituted 2-thiazo-yl, 2-pyridyl or 3-pyridazinyl. Also preferred are those compounds of formula I where $R^1$, $R^2$, $R^3$ and $R^4$ are hydrogen, ethoxy or chloro.

Although pulvinamide, pulvinanilinde and N-(napthyl)-pulvinic acid amine are known to the art (Beilstein 18:482), The N-heterocyclic pulvinic acid amides of this invention are previously unreported, novel compounds.

The compounds of formula I are generally prepared from reaction of a suitably substituted puvinic acid lactone (V) with a heterocyclic amine in a solvent such as chloroform or toluene, preferably at reflux temperature.

The pulvinic acid lactones are prepared according to the synthetic methods outlined in the following scheme:

SCHEME I

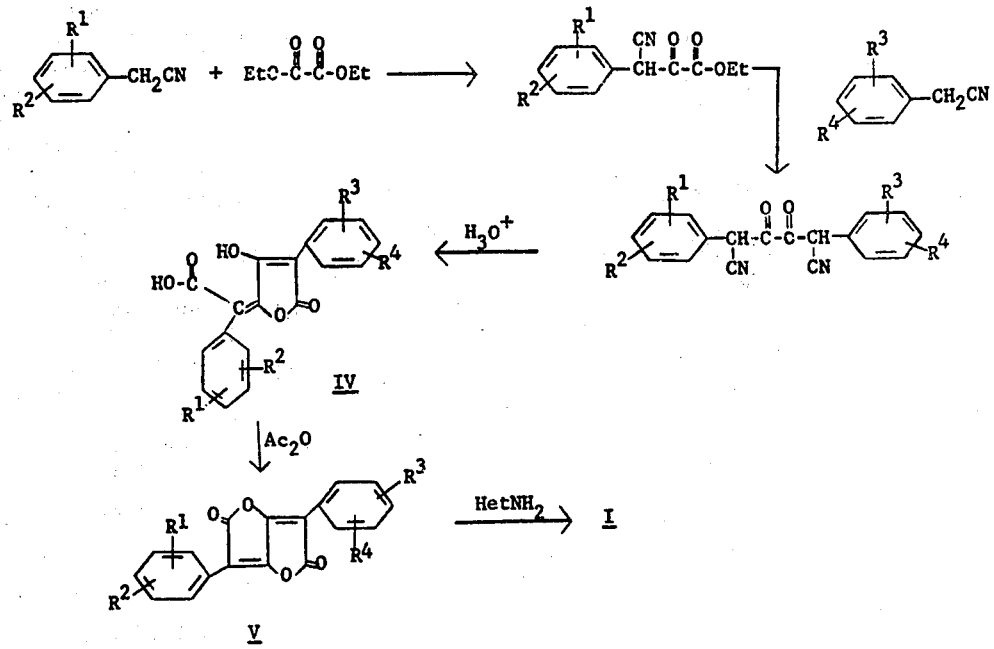

in which $R^1$, $R^2$, $R^3$, $R^4$ and Het are defined as above.

Thus, a phenylacetonitrile is condensed with ethyl oxalate in an alcoholic solution of an alkali metal lower alkoxide, such as sodium methoxide or ethoxide to give the ethyl 3-cyano-3-phenylpyruvate. This compound is further condensed with a phenylacetonitrile in an alcoholic solution of an alkali metal lower alkoxide, such as sodium methoxide or ethoxide, to yield the 2,5-diphenyl-3,4-dioxoadiponitrile. The above condensations may also be carried out using a metal hydride, such as sodium hydride, in glyme. The adiponitrile derivative is refluxed for a short period of time, for example one or two hours, in an aqueous acid solution such as a water/glacial acetic acid/concentrated sulfuric or hydrochloric acid mixture and the resulting pulvinic acid (IV) is refluxed with acetic anhydride to furnish the corresponding pulvinic acid lactone (V). The lactone ring is opened to the product amide (I) as described above by reaction with a heterocyclic amine.

When $R^1$ and $R^2$ are different from $R^3$ and $R^4$ in the above synthetic sequence, the ring opening of the dilactone (V) gives a mixture of positional isomers, namely compounds of formula I and compounds of the following formula:

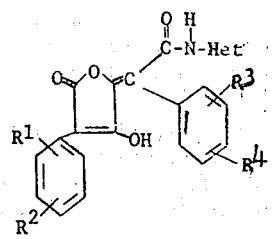

VI

The ratio of isomers is variable and depends on the nature of $R^1$, $R^2$, $R^3$ and $R^4$. The isomers can be separated by fractional crystallization and/or standard chromatographic procedures. Their identity is determined from the nuclear magnetic resonance patterns of the aromatic protons. This identification can be confirmed by degradative ozonolysis.

The anti-arthritic activity of the compounds of this invention is measured by their ability to inhibit adjuvant induced polyarthritis in rats. The novel compounds of this invention produce marked inhibition of the development of adjuvant arthritis in rats at a daily oral dose of 25 mg. per kilogram of body weight. Adjuvant arthritis in rats is produced by a single injection of 0.75 mg. of *Mycobacterium butyricum* suspended in white paraffin (N.F.) into a hindpaw (left footpad). The injected paw becomes inflamed and reaches a maximum volume in three to five days (primary lesion). The animals exhibit a decrease in body weight gain during this initial period. Adjuvant arthritis (secondary phase) occurs after a delay of approximately ten days and is characterized by inflammation of the non-injected sites (right hind leg), decrease in body weight gain and further increases in the volume of the injected hind leg. The compounds of formula I administered in the doses described above beginning on the day of adjuvant injection and continuing for 17 days thereafter, exclusive of days 4, 5, 11 and 12, protect the animals against development of both primary and secondary lesions of adjuvant arthritis.

The compounds of this invention may be administered orally or parenterally in conventional dosage unit forms by incorporating an amount sufficient to produce anti-arthritic activity, without toxic effects, with a non-toxic pharmaceutical carrier according to accepted procedures. Preferably the dosage units will contain a N-heterocyclic pulvinic acid amide of formula I in an amount of from about 10 mg. to about 50 mg. per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or an aqueous or nonaqueous liquid suspension.

the pharmaceutical dosage unit forms described hereinabove exclude simple non-sterile solutions of the active medicament in water or in common organic solvents and exclude simple aqueous suspensions of the active medicament in the absence of a suspending agent.

The method of producing anti-arthritic activity in accordance with this invention comprises administering internally to an animal organism a N-heterocyclic pulvinic acid amide of formula I, usually combined with a pharmaceutical carrier, in an amount sufficient to produce anti-arthritic activity without limiting side effects. The active medicament will be administered in a dosage unit, as described above, orally or parenterally, the oral route being preferred. Advantageously equal doses will be administered one to three times daily with the daily dosage regimen being from about 10 mg. to about 150 mg. When the method described above is carried out, anti-arthritic activity is produced with a minimum of side effects.

The pharmaceutical preparations are made following the conventional techniques of the pharmaceutical chemist involving mixing, granulating and compressing when necessary or variously mixing and dissolving the ingredients as appropriate to the desired end product.

The following examples illustrate the preparation of compounds of formula I and their incorporation into pharmaceutical compositions, and as such are not to be construed as limiting the invention set forth in the claims appended hereto. Temperatures are in degrees Centigrade unless otherwise stated.

EXAMPLE 1

N-(2-Thiazolyl)pulvinic acid amide

A mixture of 117.1 g. (1.0 mol.) of phenylacetonitrile and 326 ml. (2.4 mol.) of ethyl oxalate was added to an ethanol solution of sodium ethoxide [prepared by dissolving 23.8 g. (1.08 g. -atom) of sodium in 500 ml. of absolute ethanol] and refluxed for two hours. After cooling, diluting with 2500 ml. of water and extracting with ether, the solution was acidified with acetic acid. The solid was removed by filtration and washed with water to give ethyl 3-cyano-3-phenylpyruvate, m.p. 127°–129°.

Ethyl 3-cyano-3-phenylpyruvate (50.0 g., 0.23 mol.) and 41.0 g. (0.35 mol.) of phenylacetonitrile were added to an alcoholic solution of sodium ethoxide [prepared from 13.4 g. (0.58 g. -atom) of sodium and 360 ml. of absolute ethanol] and the resulting yellow solution was refluxed for 1.75 hours. The cooled solution was diluted with 700 ml. of water and acidified by slow addition of acetic acid. After further cooling in ice, the suspension was filtered and the solid was washed with water and dried to give 2,5-diphenyl-3,4-dioxoadiponitrile, m.p. 284°–286° (dec.).

A mixture of 30.0 g. (0.104 mol.) of 2,5-diphenyl-3,4-dioxoadiponitrile in 260 ml. of water, 380 ml. of glacial acetic acid and 190 ml. of concentrated sulfuric acid was refluxed for one hour. The suspension was cooled, poured onto 900 ml. of ice-water and the solid was removed and washed to give pulvinic acid, m.p. 215°–216.5°.

Pulvinic acid (19.0 g., 0.0616 mol.) was refluxed in 250 ml. of acetic anhydride for 15 minutes. The cooled solution was stirred into 1200 ml. of ice and water and the oily mass was crystallized by stirring in 500 ml. of ethanol. The yellow solid was removed, washed with ethanol and dried to yield pulvinic acid lactone, m.p. 221.5°–223°.

A mixture of 2.9 g. (0.01 mol.) of pulvinic acid lactone and 1.1 g. (0.011 mol.) of 2-aminothiazole in 50 ml. of chloroform was refluxed to give a homogeneous solution. The reaction mixture was cooled and the precipitated solid was collected by filtration. The filtrate was concentrated and the residue combined with the solid initially collected. The combined solid was dissolved in 5% aqueous sodium carbonate and extracted with ether. Acidification of the aqueous phase with concentrated hydrochloric acid gave the title compound as a yellow solid, m.p. 224°–226°.

EXAMPLE 2

N-(5-Chlorothiazol-2-yl)pulvinic acid amide

A mixture of 5.8 g. (0.02 mol.) of pulvinic acid lactone, 4.14 g. (0.02 mol.) of 2-amino-5-chlorothiazole hydrochloride and 1.5 g. (0.01 mol.) of potassium carbonate in 300 ml. of toluene was stirred and refluxed for 3.5 hours. The reaction mixture was cooled and the supernatant liquid decanted and chilled. The precipitated solid was collected, dissolved in chloroform and washed with water. The organic phase was dried (MgSO$_4$) and concentrated in vacuo to give the title compound, m.p. 221°–223° (toluene).

EXAMPLE 3

4,4'-Dichloro-N-(2-thiazolyl)pulvinic acid amide

A mixture of 45.3 g. (0.31 mol.) of p-chlorophenylacetonitrile and 107 g. (0.72 mol., 99 ml.) of diethyl oxalate in an alcoholic sodium ethoxide solution [prepared by dissolving 7.13 g. (0.31 g.-atom) of sodium in 120 ml. of absolute ethanol] was refluxed with stirring for two hours. The cooled reaction mixture was diluted with 700 ml. of water, acidified with acetic acid and cooled to ice bath temperature. The resulting solid was collected and recrystallized from aqueous methanol to give ethyl 3-(p-chlorophenyl)-3-cyanopyruvate, m.p. 134°–135°.

Ethyl 3-(p-chlorophenyl)-3-cyanopyruvate (40 g., 0.16 mol.) and 49.8 g. (0.33 mol.) of p-chlorophenylacetonitrile were added to an alcoholic solution of sodium ethoxide [prepared from 7.36 g. (0.32 g.-atom) of sodium and 190 ml. of absolute ethanol] and the resulting solution was refluxed for two hours. The reaction mixture was diluted with water, acidified with acetic acid and cooled (ice bath) to yield 2,5-di-(p-chlorophenyl)-3,4-dioxoadiponitrile, m.p. 280°.

A solution of 15 g. (0.042 mol.) of 2,5-di-(p-chlorophenyl)-3,4-dioxoadiponitrile in a mixture of 150 ml. of water, 210 ml. of acetic acid and 105 ml. of concentrated sulfuric acid was stirred and refluxed for two hours. The reaction mixture was diluted with 500 ml. of water and cooled to ice bath temperature to yield 4,4'-dichloropulvinic acid, m.p. 225°. The acid was refluxed in acetic anhydride to obtain the corresponding 4,4'-dichloropulvinic acid lactone.

A mixture of 3.6 g. (0.01 mol.) of 4,4'-dichloropulvinic acid lactone and 1 g. (0.01 mol.) of 2-aminothiazole in 100 ml. of toluene and 100 ml. of chloroform was refluxed for two hours. The reaction mixture was then cooled and the precipitate was collected and recrystallized from toluene-acetone to give the title compound, m.p. 220°–226°.

EXAMPLE 4

4,4'-Diethoxy-N-(2-thiazolyl)pulvinic acid amide 4,4'-Diethoxypulvinic acid lactone was prepared by substitution of an equivalent amount of 4-ethoxyphenylacetonitrile in the procedure of Example 1 for phenylacetonitrile.

A mixture of 1.4 g. (0.0037 mol.) of 4,4'-diethoxypulvinic acid lactone and 0.37 g. (0.0037 mol.) of 2-amino-thiazole in 70 ml. of toluene was refluxed for two hours. The reaction mixture was then evaporated to dryness, the residue stirred with ether, filtered, and the resulting solid was dissolved in chloroform and washed with dilute hydrochloric acid. The organic layer was dried (MgSO$_4$) and concentrated in vacuo to give the title compound, m.p. 215°–216° (methanol-acetone).

EXAMPLE 5

N-(2-Pyridyl)pulvinic acid amide

A mixture of 2.9 g. (0.01 mol.) of pulvinic acid lactone and 0.94 g. (0.01 mol.) of 2-aminopyridine in toluene was refluxed for three hours. The reaction mixture was cooled and the solid which separated was collected by filtration and recrystallized from acetonitrile to give the title compound, m.p. 206° (dec.).

EXAMPLE 6

N-(5-Chloropyrid-2-yl)pulvinic acid amide

A mixture of 1.29 g. (0.01 mol.) of 2-amino-5-chloropyridine and 2.9 g. (0.01 mol.) of pulvinic acid lactone in 100 ml. of toluene was refluxed for 12 hours. The reaction mixture was cooled, the solvent was removed in vacuo and the residue was triturated with methanol to induce crystallization. The resulting solid was collected and recrystallized from 1-chlorobutane to give the title compound, m.p. 207°–209° (dec.).

EXAMPLE 7

N-(6-Chloropyridazin-3-yl)pulvinic acid amide

A mixture of 2.9 g. (0.01 mol.) of pulvinic acid lactone and 1.30 g. (0.01 mol.) of 3-amino-6-chloropyridazine in 100 ml. of dry toluene was refluxed for three hours. The reaction mixture was cooled and the precipitate was collected by filtration. The filtrate was concentrated in vacuo, the residue was combined with the first crystal crop and the combined solid was recrystallized from 1-chlorobutane to give the title compound, m.p. 217°–219°.

EXAMPLE 8

Substitution of a substituted phenylacetonitrile listed below:
  m-chlorophenylacetonitrile
  p-methoxyphenylacetonitrile
  p-tolylacetonitrile
  (2-methoxy-5-methylphenyl)acetonitrile
  p-fluorophenylacetonitrile
  m-trifluoromethylphenylacetonitrile
  (3-chloro-4-fluorophenyl)acetonitrile
  4-biphenylacetonitrile
in the procedure described in Examples 1 or 3 for phenylace-tonitrile and p-chlorophenylacetonitrile, respectively, gives the following pulvinic acid lactones:
  3,3'-dichloropulvinic acid lactone
  4,4' dimethoxypulvinic acid lactone
  4,4'-dimethylpulvinic acid lactone
  2,2'-dimethoxy-5,5'-dimethylpulvinic acid lactone
  4,4'-difluoropulvinic acid lactone
  3,3'-bistrifluoromethylpulvinic acid lactone
  3,3'-dichloro-4,4'-difluoropulvinic acid lactone
  4,4'-diphenylpulvinic acid lactone.

Reaction of a pulvinic acid lactone listed above with 2-aminothiazole according to the procedure of Examples 1 or 3 gives the following N-(2-thiazolyl)pulvinic acid amides:
  3,3'-dichloro-N-(2-thiazolyl)pulvinic acid amide
  4,4'-dimethoxy-N-(2-thiazolyl)pulvinic acid amide
  4,4'-dimethyl-N-(2-thiazolyl)pulvinic acid amide
  2,2'-dimethoxy-5,5'-dimethyl-N-(2-thiazolyl)pulvinic acid amide
  4,4'-difluoro-N-(2-thiazolyl)pulvinic acid amide
  N-(2-thiazolyl)-3,3'-bistrifluoromethylpulvinic acid amide
  3,3'-dichloro-4,4'-difluoro-N-(2-thiazolyl)pulvinic acid amide
  4,4'-diphenyl-N-(2-thiazolyl)pulvinic acid amide.

EXAMPLE 9

Reaction of ethyl 3-(p-ethoxyphenyl)-3-cyanopyruvate with phenylacetonitrile according to the procedures described in Examples 1 and 3 and the subsequent synthetic steps as outlined above gave 4-ethoxypulvinic acid lactone.

When an equivalent amount of 4-ethoxypulvinic acid lactone was substituted in the procedure of Example 1 for pulvinic acid lactone or in the procedure of Example 3 for 4,4'-dichloropulvinic acid lactone a mixture of 4- and 4'-ethoxy-N-(2-thiazolyl)pulvinic acid amide was obtained which was separated by fractional crystallization from toluene.

EXAMPLE 10

Following the procedures outlined in Examples 1 and 3, p-methoxyphenylacetonitrile is reacted with diethyl oxalate in alcoholic sodium ethoxide solution to give ethyl 3-cyano-3-(p-methoxyphenyl)pyruvate which is then similarly reacted with phenylacetonitrile to yield 2-(p-methoxyphenyl)-5-phenyl-3,4-dioxoadiponitrile.

A solution of the adiponitrile in water, acetic acid and concentrated sulfuric acid is refluxed for two hours and the resulting crude mixture of 4-and 4'-methoxypulvinic acid is refluxed in acetic anhydride to give 4-methoxypulvinic acid lactone.

When equivalent amounts of 4-methoxypulvinic acid lactone and 2-aminothiazole are reacted according to the procedure of Examples 1 or 3, 4-methoxy-N-(2-thiazolyl)pulvinic acid amide and 4'-methoxy-N-(2-thiazolyl)pulvinic acid amide are obtained.

Similarly, by employing (3-bromo-4-methoxyphenyl)-acetonitrile in the initial reaction described above to obtain ethyl 3-cyano-3-(3'-bromo-4'-methoxyphenyl)pyruvate followed by reaction with phenylacetonitrile and the subsequent synthetic steps described above, there are prepared 3-bromo-4-methoxy-N-(2-thiazolyl)pulvinic acid amide and 3'-bromo-4'-methoxy-N-(2-thiazolyl)pulvinic acid amide.

EXAMPLE 11

Following the procedures outlined in Examples 1 and 3, 3,4-methylenedioxyphenylacetonitrile is reacted with diethyl oxalate in alcoholic sodium ethoxide solution to give ethyl 3-cyano-3-(3',4'-methylenedioxyphenyl)pyruvate which is reacted with phenylacetonitrile to yield 2-(3',4'-methylenedioxyphenyl)-5-phenyl-3,4-dioxoadiponitrile.

A solution of the adiponitrile in water, acetic acid and concentrated sulfuric acid is refluxed for two hours and the resulting crude mixture of 3,4- and 3',4'-methylenedioxypulvinic acid is refluxed in acetic anhydride to give 3,4-methylenedioxypulvinic acid lactone.

When an equivalent amount of 3,4-methylenedioxypulvinic acid lactone is substituted in the procedure of Examples 1 or 3 for pulvinic acid lactone or 4,4'-dichloropulvinic acid lactone, respectively, there are prepared 3,4-methylene-dioxy-N-(2-thiazolyl)pulvinic acid amide and 3',4'-methylene-dioxy-N-(2-thiazolyl)pulvinic acid amide.

EXAMPLE 12

3,4,3',4'-Bismethylenedioxy-N-(2-thiazolyl)pulvinic acid amide

By reacting ethyl 3-cyano-3-(3',4'-methylenedioxyphenyl)pyruvate with 3,4-methylenedioxyphenylacetonitrile following procedures set forth in Examples 1 and 3 above there is obtained 2,5-di-(3',4'-methylenedioxyphenyl)-3,4-dioxoadiponitrile.

The adiponitrile is refluxed in water, acetic acid and concentrated sulfuric acid to yield 3,4,3',4'-bismethylenedioxypulvinic acid which is treated with acetic anhydride to give 3,4,3',4'-bismethylenedioxypulvinic acid lactone.

Reaction of the lactone with 2-aminothiazole as described in Examples 1 and 3 gives the title compound.

EXAMPLE 13

A mixture of 117.1 g. (1.0 mol.) of phenylacetonitrile and 326 ml. (2.4 mol.) of ethyl oxalate was added to an ethanol solution of sodium ethoxide [prepared by dissolving 23.8 g. (1.08 g.-atom) of sodium in 500 ml. of absolute ethanol] and refluxed two hours. After cooling, diluting with 2500 ml. of water and extracting with ether, the solution was acidified with acetic acid. The solid was removed and washed with water to give ethyl 3-cyano-3-phenylpyruvate, m.p. 127°–129°.

Ethyl 3-cyano-3-phenylpyruvate (13.0 g., 0.06 mol.) was slowly added to a mixture of 11.6 g. (0.06 mol.) of p-biphenylacetonitrile and 8.44 g. (0.18 mol.) of sodium hydride in 40 ml. of diglyme at a temperature below 0°. The mixture was permitted to warm and several drops of methanol were added to initiate the reaction. The mixture was allowed to stand at 25° for 12 hours, cooled and diluted with 150 ml. of water. The mixture was then extracted with ether and the aqueous layer was acidified with acetic acid to give 2-(4'-biphenyl)-5-phenyl-3,4-dioxoadiponitrile as a yellow solid.

A mixture of 16.9 g. of 2-(4'-biphenyl)-5-phenyl-3,4-dioxoadiponitrile in 95 ml. of water, 140 ml. of glacial acetic acid and 70 ml. of concentrated sulfuric acid was refluxed for one hour. The suspension was cooled, poured onto 800 ml. of ice water and the solid was removed and washed with water to give 4'-phenylpulvinic acid.

4'-Phenylpulvinic acid (23.0 g.) was refluxed in 300 ml. of acetic anhydride for 15 minutes. The cooled solution was stirred into 1200 ml. of ice and water and the oily mass was crystallized by stirring in 500 ml. of ethanol. The brown solid was removed, washed with ethanol and dried to yield 4-phenylpulvinic acid lactone.

Substitution of an equivalent amount of 4-phenylpulvinic acid lactone in the procedure of Example 1 or Example 3 for pulvinic acid lactone or 4,4'-dichloropulvinic acid lactone gives 4'-phenyl-N-(2-thiazolyl)pulvinic acid amide.

Similarly, p-biphenylacetonitrile is reacted with ethyl oxalate to give ethyl 3-cyano-3-biphenylpyruvate which in turn is reacted with phenylacetonitrile followed by the above subsequent synthetic steps to yield 4-phenyl-N-(2-thiazolyl)pulvinic acid amide.

EXAMPLE 14

By employing the procedures described in Example 1, p-fluorophenylacetonitrile is reacted with diethyl oxalate in alcoholic sodium ethoxide to give ethyl 3-cyano-3-(p-fluoro-phenyl)pyruvate. The latter is reacted with phenylacetonitrile and subsequent synthetic steps yield 4-fluoropulvinic acid lactone. The lactone ring is opened with 2-aminothiazole as described above to give 4-fluoro-N-(2-thiazolyl)pulvinic acid amide.

Similarly, by utilizing m-trifluoromethylphenylacetonitrile as the starting material in the initial reaction as described above, there is ultimately produced N-(2-thiazolyl)-3-trifluoromethylpulvinic acid amide.

In like manner, when p-phenoxyphenylacetonitrile is used as the starting material in the initial reaction as described above, there is ultimately produced 4-phenoxy-N-(2-thiazolyl)pulvinic acid amide.

EXAMPLE 15

3,4,3',4'-Tetraethoxy-N-(2-thiazolyl)pulvinic acid amide

By following the procedures outlined in Examples 1 and 3, 3,4-diethoxyphenylacetonitrile is reacted with diethyl oxalate in alcoholic sodium ethoxide solution to give ethyl 3-cyano-3-(3',4'-diethoxyphenyl)pyruvate. This compound is similarly reacted with 3,4-diethoxyphenylacetonitrile which results in the formation of 2,5-di-(3',4'-diethoxyphenyl)-3,4-dioxoadiponitrile.

The latter is refluxed with water, acetic acid and sulfuric acid to give 3,4,3',4'-tetraethoxypulvinic acid which is treated with acetic anhydride to give the corresponding acid lactone.

Reaction of the lactone with 2-aminothiazole as described in Examples 1 or 3 above gives the title compound.

EXAMPLE 16

To a solution of 6.6 g. (0.044 mol.) of p-chlorophenylacetonitrile and 20 ml. of dry glyme was added 6.2 g. (0.13 mol.) of sodium hydride (50% in oil). Ethyl 3-cyano-3-phenylpyruvate (9.55 g., 0.044 mol.) was added in portions at −10° and the reaction mixture was stirred at 25° for 12 hours. The mixture was diluted with 150 ml. of water, extracted with ether, acidified with 15 ml. of acetic acid and the solid was collected by filtration to yield 2-(p-chloro-phenyl)-5-phenyl-3,4-dioxoadiponitrile, m.p. 210° (dec.).

A solution of the adiponitrile in water, acetic acid and concentrated sulfuric acid was refluxed for two hours and the resulting crude mixture of 4- and 4'-chloropulvinic acid was refluxed in acetic anhydride to give 4-chloro-pulvinic acid lactone, m.p. 213°–214°.

Reaction of 4-chloropulvinic acid lactone and 2-aminothiazole according to the procedure described in Examples 1 or 3 gives 4-chloro-N-(2-thiazolyl)pulvinic acid amide.

Similarly, by using 3,4-dichlorophenylacetonitrile in the initial reaction described above to obtain 2-(3',4'-dichlorophenyl)-5-phenyl-3,4-dioxoadiponitrile followed by the subsequent synthetic steps, there is prepared 3,4-di-chloropulvinic acid lactone.

Treatment of 3,4-dichloropulvinic acid lactone with 2-aminothiazole as described in Examples 1 or 3 gives 3,4-dichloro-N-(2-thiazolyl)pulvinic acid amide.

EXAMPLE 17

Following the procedures of Examples 1 and 3, 2-(p-tolyl)-5-phenyl-3,4-dioxoadiponitrile is prepared from p-tolylacetonitrile and phenylacetonitrile. The adiponitrile was refluxed with water, acetic acid and concentrated sulfuric acid to give a crude mixture of 4- and 4'-methylpulvinic acid. The latter was refluxed in acetic anhydride to give 4-methylpulvinic acid lactone, m.p. 211–213°.

Substitution of 4-methylpulvinic acid lactone in the procedure of Example 1 for pulvinic acid lactone or Example 3 for 4,4'-dichloropulvinic acid lactone gives 4-methyl-N-(2-thiazolyl)pulvinic acid amide and 4'-methyl-N-(2-thiazolyl)pulvinic acid amide.

EXAMPLE 18

When an equivalent amount of p-n-butoxyphenylacetonitrile is substituted in the procedure of Example 1 for phenylacetonitrile and the ethyl 3-cyano-3-(p-n-butoxyphenyl)pyruvate thus obtained is similarly reacted with phenylacetonitrile, the product converted to the pulvinic acid and subsequently lactonized, 4-n-butoxypulvinic acid lactone is obtained.

Reaction of 4-n-butoxypulvinic acid lactone with 2-aminothiazole as previously described gives 4'-n-butoxy-N-(2-thiazolyl)pulvinic acid amide and 4-n-butoxy-N-(2-thiazolyl)pulvinic -thiazolyl)pulvinic amide.

Similarly, by employing (3-chloro-2-methylphenyl)-acetonitrile as the starting material in the above synthetic sequence there are obtained as final products, 3-chloro-2-methyl-N-(2thiazolyl)pulvinic acid amide and 3'-chloro-2'-methyl-N-(2-thiazolyl)pulvinic acid amide.

EXAMPLE 19   4,4'-Dihydroxy-N-(2-thiazolyl)pulvinic acid amide 2,5-Di-(p-methoxyphenyl)-3,4-dioxoadiponitrile (10.0 g., 0.029 mol.) was refluxed in 500 ml. of acetic acid and 62 ml. of hydrogen iodide for 1.5 hours. The reaction mixture was cooled, diluted with 150 ml. of water and sodium bisulfite was added until the solution became light red. The reaction mixture was concentrated in vacuo to about 200 ml., treated with about 400 ml. of acetic anhydride in portions (until no violent bubbling occurred) and refluxed for 15 minutes. The mixture was cooled, poured onto 600 ml. of ice and crystallized by addition of methanol. The solid was collected by filtration, washed with methanol and dried to give 4,4'-diacetoxypulvinic acid lactone.

Treatment of 4,4'-diacetoxypulvinic acid lactone with 2-aminothiazole as previously described followed by hydrolysis of the product 4,4'-diacetoxy-N-(2-thiazolyl)pulvinic acid amide with 5.4 g. (0.1 mol.) of sodium methoxide in 60 ml. of methanol at 25° for 30 minutes gives the title compound.

EXAMPLE 20

3-Chloro-4'-hydroxy-N-(2-thiazolyl)pulvinic acid amide

When ethyl 3-(p-methoxyphenyl)-3-cyanopyruvate and m-chlorophenylacetonitrile are reacted according to the procedure described in Examples 1 and 3 and the resulting adiponitrile is substituted in the procedure of Example 19 for 2,5-di-(p-methoxyphenyl)-3,4-dioxoadiponitrile, 3-chloro-4'-acetoxypulvinic acid lactone is obtained.

Treatment of the lactone with 2-aminothiazole followed by hydrolysis of the product 3-chloro-4'-acetoxy-N-(2-thiazolyl)pulvinic acid amide with sodium methoxide in methanol as described in the procedure of Example 19 gives the title compound.

EXAMPLE 21

When an equivalent amount of 2-amino-5-bromopyridine is substituted in the procedure of Example 6 for 2-amino-5-chloropyridine, N-(5-bromopyrid-2yl)pulvinic acid amide is obtained.

Similarly, substitution of an equivalent amount of 2-amino-4-methylpyridine in the procedure of Example 6 for 2-amino-5-chloropyridine gives N-(4-methylpyrid-2-yl)pulvinic acid amide.

Likewise, reaction of 2-amino-5-bromopyridine and 2-amino-4-methylpyridine with the other pulvinic acid lactones disclosed herein gives the corresponding N-(5-bromopyrid-2-yl)- and N-(4-methylpyrid-2-yl) amides.

EXAMPLE 22

When an equivalent amount of a heterocyclic amine listed below:
 2-amino5-bromothiazole
 2-amino-4,5-dimethylthiazole
 2-amino-4-methylthiazole
 2-aminooxazole
 2-aminoimidazole
 2-amino-4,5-dimethylimidazole is substituted in the procedure of Example 1 or 3 for 2-amino-thiazole, the following N-heterocyclic pulvinic acid amides are prepared:
 N-(5-bromothiazol-2-yl)pulvinic acid amide
 N-(4,5-dimethylthiazol-2-yl)pulvinic acid amide
 N-(4-methylthiazol-2-yl)pulvinic acid amide
 N-(2-oxazolyl)pulvinic acid amide
 N-(2-imidazolyl)pulvinic acid amide
 N-(4,5-dimethylimidazol-2-yl)pulvinic acid amide.

Similarly, the heterocyclic amines listed above may be reacted with the other pulvinic acid lactones disclosed herein to give the corresponding N-heterocyclic pulvinic acid amides.

EXAMPLE 23

Substitution of a benzheterocyclic amine listed below:
 2-aminobenzimidazole
 2-aminobenzothiazole
 2-aminobenzoxazole in the procedure of Example 1 or 3 for 2-aminothiazole gives the following N-heterocyclic pulvinic acid amides, respectively:
 N-(2-benzimidazolyl)pulvinic acid amide
 N-(2-benzothiazolyl)pulvinic acid amide
 N-(2-benzoxazolyl)pulvinic acid amide.

In like manner, the benzheterocyclic amines listed above may be reacted with the other pulvinic acid lactones described herein to give the corresponding N-heterocyclic pulvinamides.

EXAMPLE 24

N-(2-Thiazolinyl)pulvinic acid amide is prepared by reaction of equivalent amounts of pulvinic acid lactone and 2-amino-2-thiazoline by the procedure described in Example 1 or Example 3.

In the same manner, N-(6-methylpyridazin-3-yl)pulvinic acid amide is obtained by substitution of an equivalent amount of 3-amino-6-methylpyridazine in the procedure of Example 7 for 3-amino-6-chloropyridazine.

2-Amino-2-thiazoline and 3-amino-6-methylpyridazine may be reacted with the other pulvinic acid lactones disclosed herein to give the corresponding N-(2-thiazolinyl) and N-(6-methylpyridazin-3-yl) amides.

EXAMPLE 25

When an equivalent amount of 3-trifluoromethyl-phenylacetonitrile is substituted in the procedure of Example 1 for phenylacetonitrile, and the ethyl 3-cyano-3-(3'-trifluoromethylphenyl)pyruvate thus obtained is similarly reacted with p-ethoxyphenylacetonitrile, the product converted to the pulvinic acid and subsequently lactonized, there is obtained 4-ethoxy-3'-trifluoromethylpulvinic acid lactone.

Reaction of 4-ethoxy-3'-trifluoromethylpulvinic acid lactone with 2-aminothiazole as previously described gives 4-ethoxy- 3'-trifluoromethyl-N-(2-thiazolyl)pulvinic acid amide and 4'-ethoxy-3-trifluoromethyl-n-(2-thiazolyl)-pulvinic acid amide.

EXAMPLE 26

Substitution of an equivalent amount of 3trifluoromethylphenylacetonitrile in the procedure of Example 1 for phenylacetonitrile followed by reaction of the resulting 3-cyano-3-(3'-trifluoromethylphenyl)-pyruvate with p-acetoxy-phenylacetonitrile with subsequent conversion to the pulvinic acid and lactonization gives 4-acetoxy-3'-trifluoromethylpulvinic acid lactone.

Treatment of 4-acetoxy-3'-trifluoromethylpulvinic acid lactone with 2-aminothiazole followed by hydrolysis of the product with sodium methoxide in methanol as described in the procedure of Example 19 gives 4-hydroxy-3'-trifluoromethyl-N-(2-thiazolyl)pulvinic acid amide and 4'-hydroxy-3-trifluoromethyl-N-(2-thiazolyl)pulvinic acid amide.

EXAMPLE 27

| Ingredients | Mg./Tablet |
| --- | --- |
| 4,4'-Diethoxy-N-(2-thiazolyl)-pulvinic acid amide | 10 |
| Calcium sulfate, dihydrate | 150 |
| Sucrose | 25 |
| Starch | 15 |
| Talc | 5 |
| Stearic Acid | 3 |

The sucrose, calcium sulfate and 4,4'-diethoxy-N-(2-thiazolyl)-pulvinic acid amide are thoroughly mixed and granulated with hot 10% gelatin solution. The wetted mass is passed through a No. 6 mesh screen directly onto drying trays. The granules are dried at 120°F. and passed through a No. 20 mesh screen, mixed with the starch, talc and stearic acid and compressed into tablets.

Similarly, the other N-heterocyclic pulvinic acid amides disclosed herein may be formulated into tablets.

EXAMPLE 28

| Ingredients | Mg./Capsule |
| --- | --- |
| N-(2-thiazolyl)pulvinic acid amide | 50 |
| Magnesium stearate | 5 |
| Lactose | 350 |

The above ingredients are screened through a No. 40 mesh screen, mixed and filled into No. 0 hard gelatin capsules.

Similarly, the other N-heterocyclic pulvinic acid amides disclosed herein may be formulated into capsules.

What is claimed is:

1. A pharmaceutical composition having anti-arthritic activity, in dosage unit form, comprising a pharmaceutical carrier and an effective but nontoxic amount of a compound of the formula:

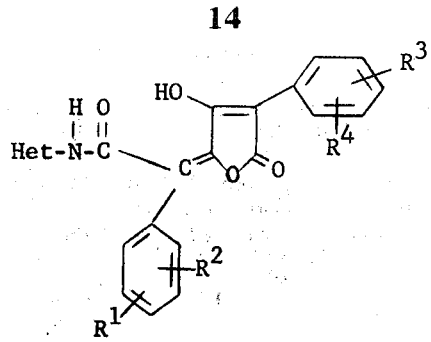

in which:
$R^1$, $R^2$, $R^3$ and $R^4$ are each hydrogen, lower alkyl of from one to four carbon atoms, lower alkoxy of from one to four carbon atoms, phenyl, phenoxy, halogen, trifluoromethyl, hydroxy or, taken together in adjacent positions, methylenedioxy; and
Het is a heterocyclic moiety of the formula:

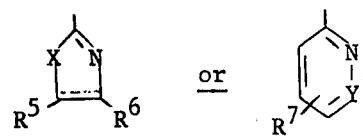

in which:
X is S, NH or O;
Y is N or CH;
$R^5$ and $R^6$ are hydrogen, methyl or halogen, or together form a 1,2-benzo radical;
$R^7$ is hydrogen, methyl or halogen; and
═ indicates an optional double bond.

2. The composition of claim 1 in which Het is substituted or unsubstituted 2-thiazolyl, 2-pyridyl or 3-pyridazinyl.

3. The composition of claim 2 in which $R^1$, $R^2$, $R^3$ and $R^4$ are hydrogen, ethoxy or chloro.

4. The composition of claim 3 in which the active medicament is 4,4'-diethoxy-N-(2-thiazolyl)-pulvinic acid amide.

5. The composition of claim 3 in which the active medicament is N-(5-chlorothiazol-2-yl)pulvinic acid amide.

6. The composition of claim 3 in which the active medicament is N-(2-thiazolyl)pulvinic acid amide.

7. The composition of claim 3 in which the active medicament is 4-ethoxy-N-(2-thiazolyl)pulvinic acid amide.

8. The composition of claim 3 in which the active medicament is 4'-ethoxy-N-(2-thiazolyl)pulvinic acid amide.

9. The composition of claim 1 in which the active medicament is in an amount of from 10 mg. to about 50 mg. per dosage unit.

10. The method of producing anti-arthritic activity which comprises administering internally to an animal organism in an amount sufficient to produce said activity a compound as defined in claim 1.

11. The method of claim 10 in which Het is substituted or unsubstituted 2-thiazolyl, 2-pyridyl or 3-pyridazinyl.

12. The method of claim 11 in which $R^1$, $R^2$, $R^3$ and $R^4$ are hydrogen, ethoxy or chloro.

13. The method of claim 12 in which the active medicament is 4,4'-diethoxy-N-(2-thiazolyl)pulvinic acid amide.

14. The method of claim 12 in which the active medicament is N-(5-chlorothiazol-2-yl)pulvinic acid amide.

15. The method of claim 12 in which the active medicament is N-(2-thiazolyl)pulvinic acid amide.

16. The method of claim 12 in which the active medicament is 4-ethoxy-N-(2-thiazolyl)pulvinic acid amide.

17. The method of claim 12 in which the active medicament is 4'-ethoxy-N-(2-thiazolyl)pulvinic acid amide.

18. The method of claim 10 in which the active medicament is administered in a daily dosage regimen of about 10 mg. to about 150 mg.

* * * * *

UNITED STATES PATENT OFFICE
CERTIFICATE OF CORRECTION

PATENT NO. : 3,947,580
DATED : March 30, 1976
INVENTOR(S) : Joseph Weinstock

It is certified that error appears in the above-identified patent and that said Letters Patent are hereby corrected as shown below:

Column 2, line 28, "The" should read --the--

Column 6, line 20, "225°" should read --255°--

Column 7, line 27, "nylace-tonitrile" should read --nylacetonitrile--

Column 11, lines 9 and 10, should read "butoxy-N-(2-thiazolyl)pulvinic acid amide."

Column 13, line 9, "3tri-" should read --3-tri--.

Signed and Sealed this

Third Day of August 1976

[SEAL]

Attest:

RUTH C. MASON
*Attesting Officer*

C. MARSHALL DANN
*Commissioner of Patents and Trademarks*